US009498170B2

(12) United States Patent
Schwarzbach

(10) Patent No.: US 9,498,170 B2
(45) Date of Patent: Nov. 22, 2016

(54) APPARATUS FOR HOLDING AND POSITIONING X-RAY FILM, PHOTOSTIMULABLE PHOSPHOR PLATES OR DIGITAL SENSORS WHILE TAKING DENTAL RADIOGRAPHS

(71) Applicant: Louis Eliot Schwarzbach, Northridge (CA)

(72) Inventor: Louis Eliot Schwarzbach, Northridge (CA)

( * ) Notice: Subject to any disclaimer, the term of this patent is extended or adjusted under 35 U.S.C. 154(b) by 233 days.

(21) Appl. No.: 14/284,214

(22) Filed: May 21, 2014

(65) Prior Publication Data

US 2015/0016588 A1    Jan. 15, 2015

Related U.S. Application Data

(60) Provisional application No. 61/855,788, filed on May 23, 2013.

(51) Int. Cl.
*A61B 6/08* (2006.01)
*A61B 6/14* (2006.01)
*A61B 6/00* (2006.01)

(52) U.S. Cl.
CPC ............. *A61B 6/145* (2013.01); *A61B 6/4435* (2013.01); *A61B 6/08* (2013.01)

(58) Field of Classification Search
CPC ....... A61B 6/08; A61B 6/145; A61B 6/4435
See application file for complete search history.

(56) References Cited

U.S. PATENT DOCUMENTS

| 1,923,669 | A | * | 8/1933 | Harrison | G03B 42/042 378/170 |
| 3,003,062 | A | * | 10/1961 | Updegrave | G03B 42/042 24/702 |
| 3,617,742 | A | * | 11/1971 | Schulman | A61B 6/14 378/170 |
| 4,144,460 | A | * | 3/1979 | Norman | A61B 6/14 378/170 |
| 6,190,042 | B1 | * | 2/2001 | Dove | A61B 6/145 378/167 |

OTHER PUBLICATIONS

Dias et al., Reliability and accuracy of a radiographic analysis method for posterior maxillary mini-implant location, Feb. 2012, Journal of Applied Oral Science, vol. 20, No. 1, pp. 99-103.*

* cited by examiner

*Primary Examiner* — David J Makiya
*Assistant Examiner* — John Corbett
(74) *Attorney, Agent, or Firm* — Buchalter Nemer

(57) ABSTRACT

A positioner arm for positioning an imaging material, an imaging material holder, an aiming device or a combination thereof is disclosed that includes at least one positioning arm having a first end and a second end, wherein each arm comprises at least two fixed arm angles and wherein at least one angle is not a 90 degree angle. Methods of obtaining non-right angle views of a patient during x-ray imaging of the patient's mouth are also disclosed that include: providing a positioner arm for positioning an imaging material, an imaging material holder, an aiming device or a combination thereof, wherein the positioner arm comprises at least one positioning arm having a first end and a second end, wherein each arm comprises at least two fixed arm angles, and wherein at least one angle is not a 90 degree angle; coupling the positioner arm with an imaging material, an imaging material holder, an aiming device or a combination thereof; and imaging the patient's mouth, wherein the imaging is taken at a non-right angle.

20 Claims, 8 Drawing Sheets

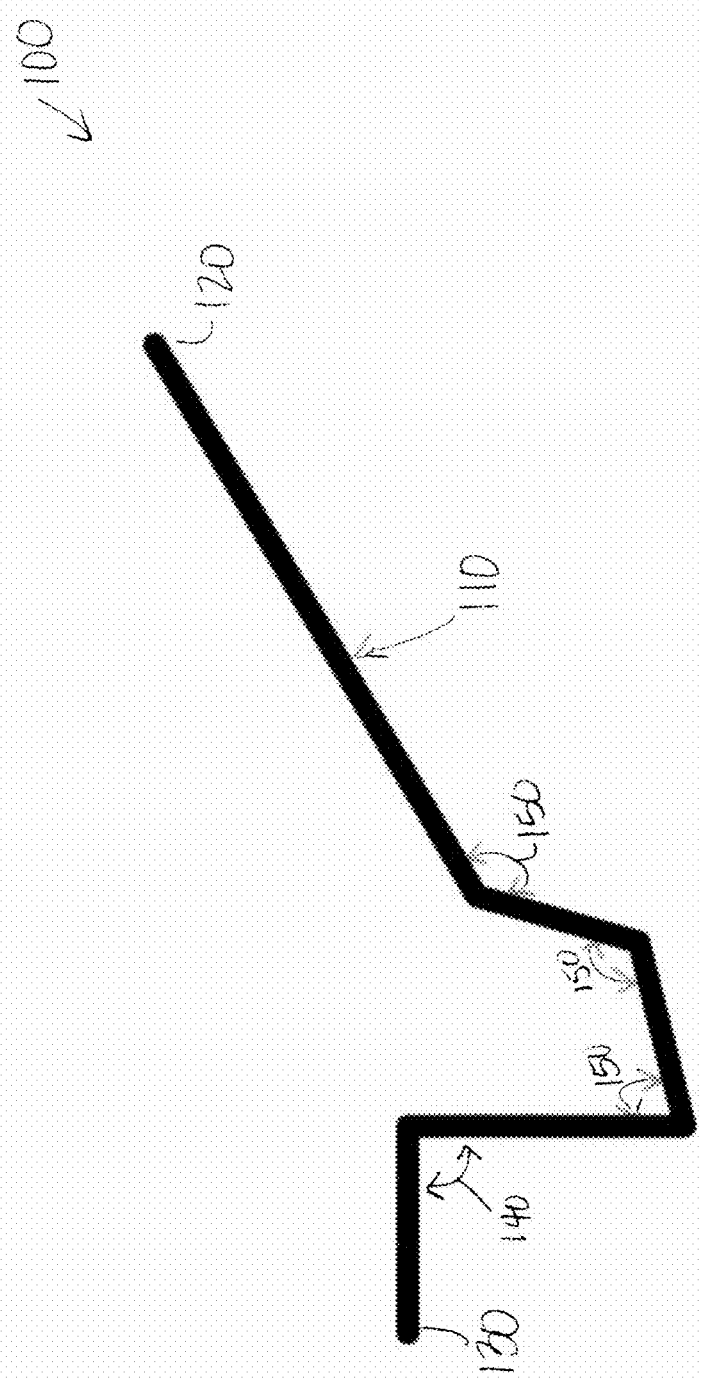

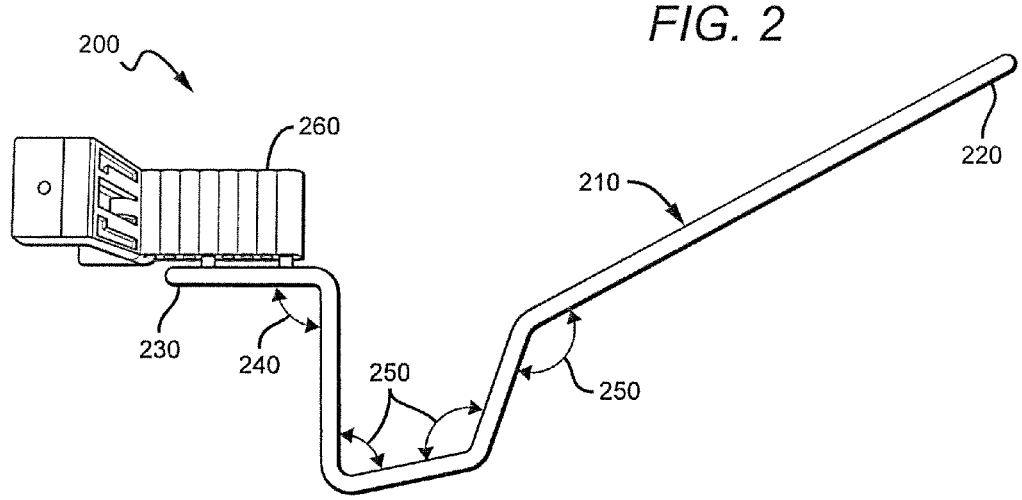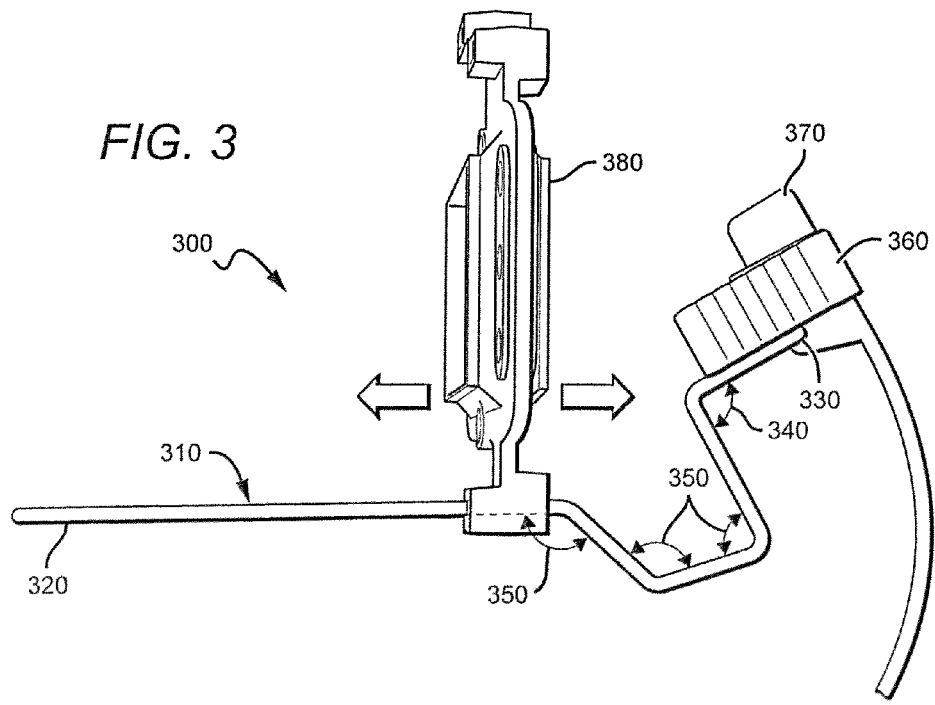

APPARATUS FOR HOLDING AND POSITIONING X-RAY FILM, PHOTOSTIMULABLE PHOSPHOR PLATES OR DIGITAL SENSORS WHILE TAKING DENTAL RADIOGRAPHS

This U.S. Utility Application claims priority to U.S. Provisional Application Ser. No. 61/855,788, which was filed on May 23, 2013 and is entitled "Means of Holding and Positioning X-Ray Film, Photostimulable Phosphor Plates or Sensors While Taking Dental Radiographs" and which is commonly-owned and incorporated herein in its entirety by reference.

FIELD OF THE SUBJECT MATTER

The field of the subject matter is dental radiographs, particularly to satisfactorily holding the x-ray film, photostimulable phosphor plate or digital sensor in the correct position while taking the image.

BACKGROUND

It is well known that dental x-rays are an important part of the examination and treatment of teeth and surrounding structures including the mandible and maxilla. Proper positioning of the x-ray units in relationship to the film/plate/sensor is important to obtaining the required information.

It is also well known that many techniques in film/plate/sensor x-ray unit positioning have been developed over the years. X-ray positioners have been used to enhance the image information. Most positioning devices aid in providing a right angle relationship in a horizontal plane of film/plate/sensor and x-ray tube (unit). Moveable angles have been described: however, most dental x-rays are 2-dimensional views.

It is also well known that off angle (non-right angle) x-ray views can provide additional information useful in the examination and treatment of the dentition and supporting structures, which is particularly true where elements of the targeted tooth/teeth are hidden behind other elements of that tooth, that is, superimposed structures. If an x-ray is taken at an off-angle relative to the straight-on (right angle) view of the tooth, it is possible to get images of important elements that will increase the potential for positive results of the planned procedure or diagnosis. No satisfactory apparatus or methods are currently available to hold the x-ray film at the desired fixed off-angle (non-right angle).

There are a number of patents, patent applications and journal articles that teach and disclose these conventional methods and apparatus; however, none of the patents, patent applications or journal articles reviewed to date discuss producing and utilizing an apparatus and related methods that will: a) hold x-ray film or another imaging medium at a desired and fixed off-angle or a non-right angle in order to provide necessary information for the dental professional, and b) consistently and reliably line up the x-ray film or imaging medium with the x-ray source (tube head), so as to provide the image information.

To this end, it would be desirable to form and utilize an apparatus and related methods that will a) hold x-ray film at a desired and fixed off-angle or a non-right angle in order to provide necessary information for the dental professional, and b) consistently and reliably line up the x-ray film with the x-ray source (tube head), so as to provide the image information.

SUMMARY OF THE SUBJECT MATTER

A positioner arm for positioning an imaging material, an imaging material holder, an aiming device or a combination thereof is disclosed that includes at least one positioning arm having a first end and a second end, wherein each arm comprises at least two fixed arm angles and wherein at least one angle is not a 90 degree angle.

Methods of obtaining non-right angle views of a patient during x-ray imaging of the patient's mouth are also disclosed that include: providing a positioner arm for positioning an imaging material, an imaging material holder, an aiming device or a combination thereof, wherein the positioner arm comprises at least one positioning arm having a first end and a second end, wherein each arm comprises at least two fixed arm angles, and wherein at least one angle is not a 90 degree angle; coupling the positioner arm with an imaging material, an imaging material holder, an aiming device or a combination thereof; and imaging the patient's mouth, wherein the imaging is taken at a non-right angle.

BRIEF DESCRIPTION OF THE FIGURES

FIG. 1 shows a distal view positioner arm for film, psp plate or sensor endodontic biteblock. FIG. 1 also shows a positioner arm system 100 for positioning an imaging material (not shown) that includes one positioning arm 110 having a first end 120 and a second end 130, wherein the arm 110 comprises fixed arm angles that are at 90 degree angles 140 and fixed arm angles that are not at a 90 degree angle 150.

FIG. 2 shows a distal view positioner arm for film, psp plate or sensor endodontic biteblock with two additional extension rods. FIG. 2 also shows a positioner arm system 200 for positioning an imaging material (not shown) held by an imaging material holder 260 that includes one positioning arm 210 having a first end 220 and a second end 230, wherein the arm 210 comprises fixed arm angles that are at 90 degree angles 240 and fixed arm angles that are not at a 90 degree angle 250.

FIG. 3 shows a distal view positioner arm for film, psp plate or sensor endodontic biteblock. FIG. 3 also shows a positioner arm system 300 for positioning an imaging material 370 held by an imaging material holder 360 that includes one positioning arm 310 having a first end 320 and a second end 330, wherein the arm 310 comprises fixed arm angles that are at 90 degree angles 340 and fixed arm angles that are not at a 90 degree angle 350. This Figure also shows an aiming ring 380 that is designed to be removable from the arm 310 and slidable back and forth along the arm 310.

FIG. 4 also shows a positioner arm system 400 for positioning an imaging material 470 in the mouth of a patient 490 held by an imaging material holder 460 that includes one positioning arm 410 having a first end 420 and a second end (not shown), wherein the arm 410 comprises fixed arm angles that are at 90 degree angles 440 and fixed arm angles that are not at a 90 degree angle 450. This Figure also shows an aiming ring 480 that is designed to be removable from the arm 410 and slidable back and forth along the arm 410.

Figure 6:
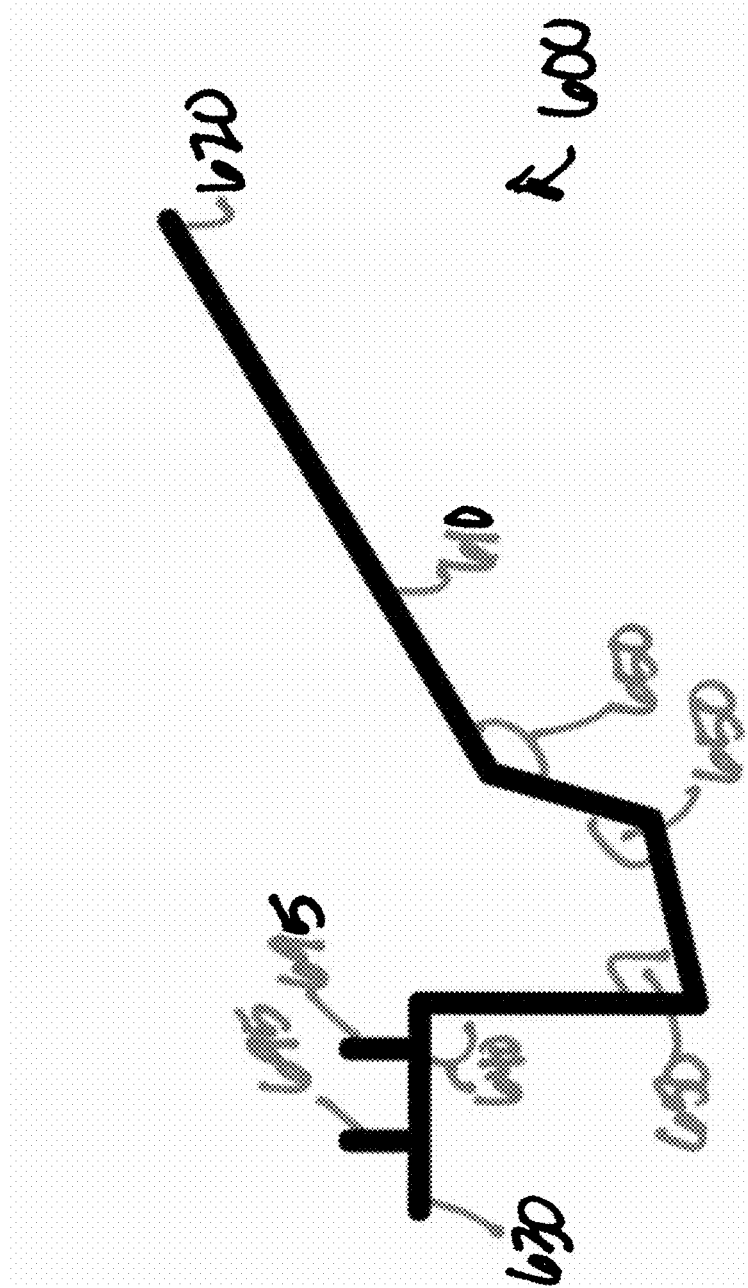

FIG. 6 shows distal view of a positioner arm system 600 for positioning an imaging material (not shown) that includes one positioning arm 610 having a first end 620 and a second end 630, wherein the arm 610 comprises fixed arm angles that are at 90 degree angles 640 and fixed arm angles that are not at a 90 degree angle 650. This embodiment also shows two extension rods 695 that are located near the second end 630.

Figure 7:
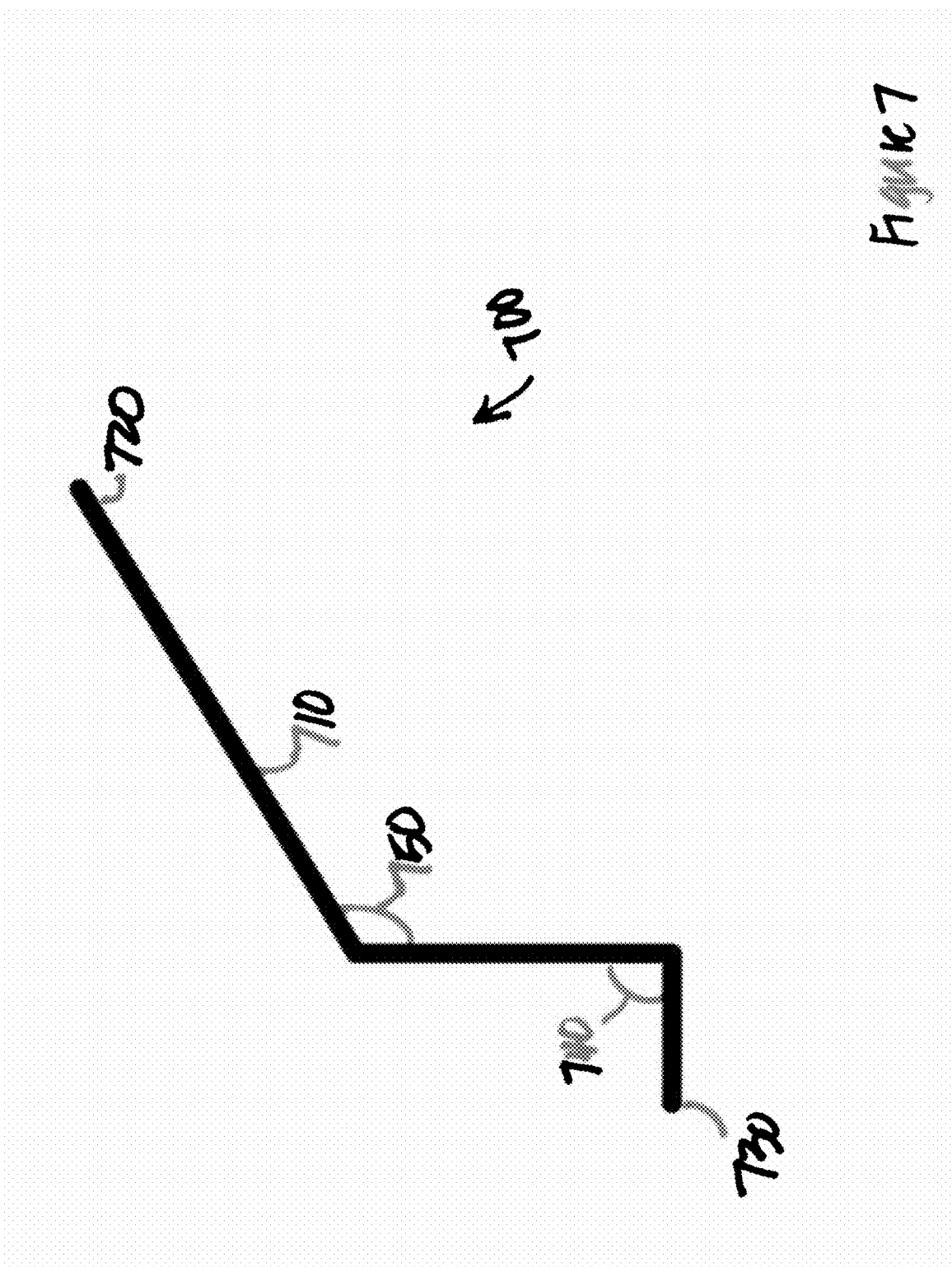

FIG. 7 shows another contemplated positioner arm system 700 (mesial view) for positioning an imaging material (not shown) that includes one positioning arm 710 having a first end 720 and a second end 730, wherein the arm 710 comprises fixed arm angles that are at 90 degree angles 740 and fixed arm angles that are not at a 90 degree angle 750.

Figure 8:
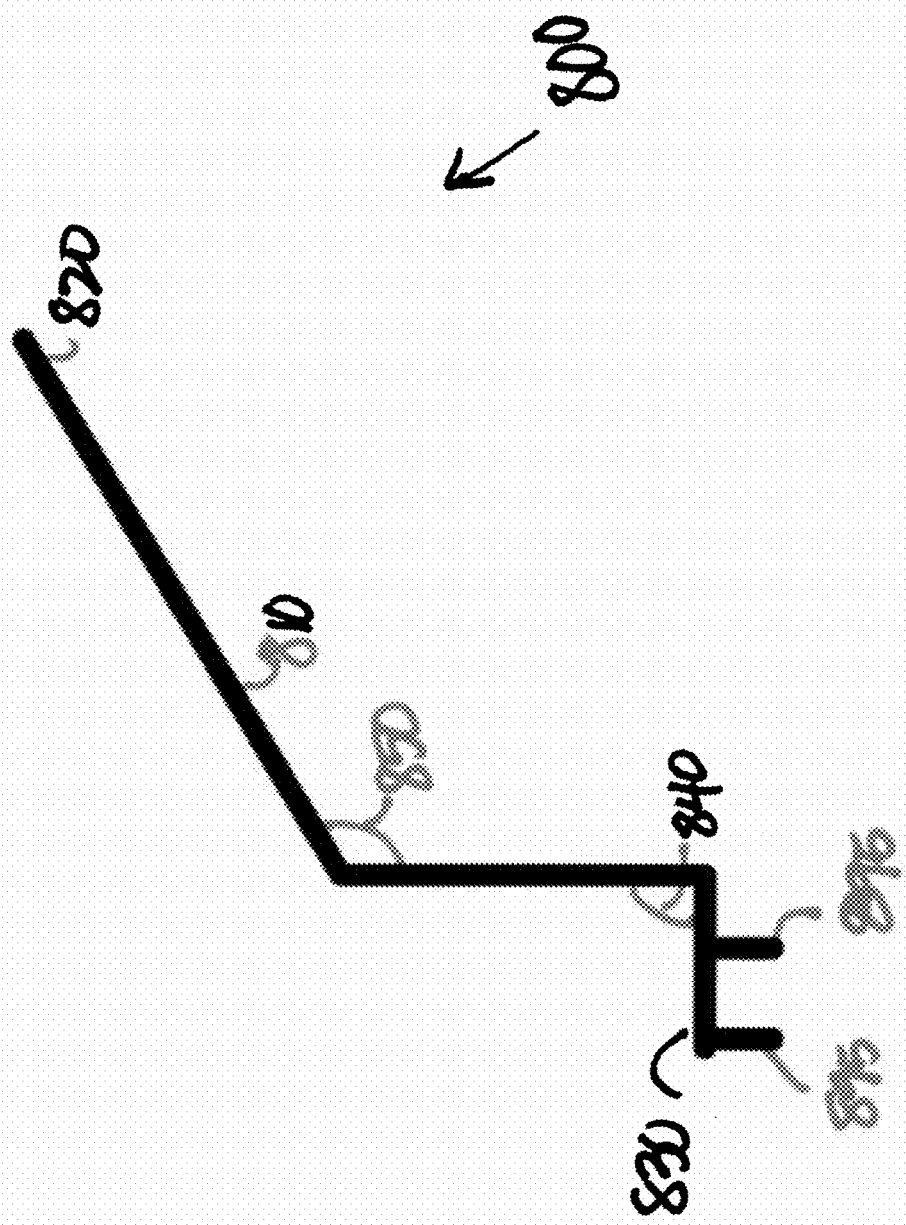

FIG. 8 shows a positioner arm system 800 (mesial view) for positioning an imaging material (not shown) that includes one positioning arm 810 having a first end 820 and a second end 830, wherein the arm 810 comprises fixed arm angles that are at 90 degree angles 840 and fixed arm angles that are not at a 90 degree angle 850. This embodiment also shows two extension rods 895 that are located near the second end 830.

Figure 9:
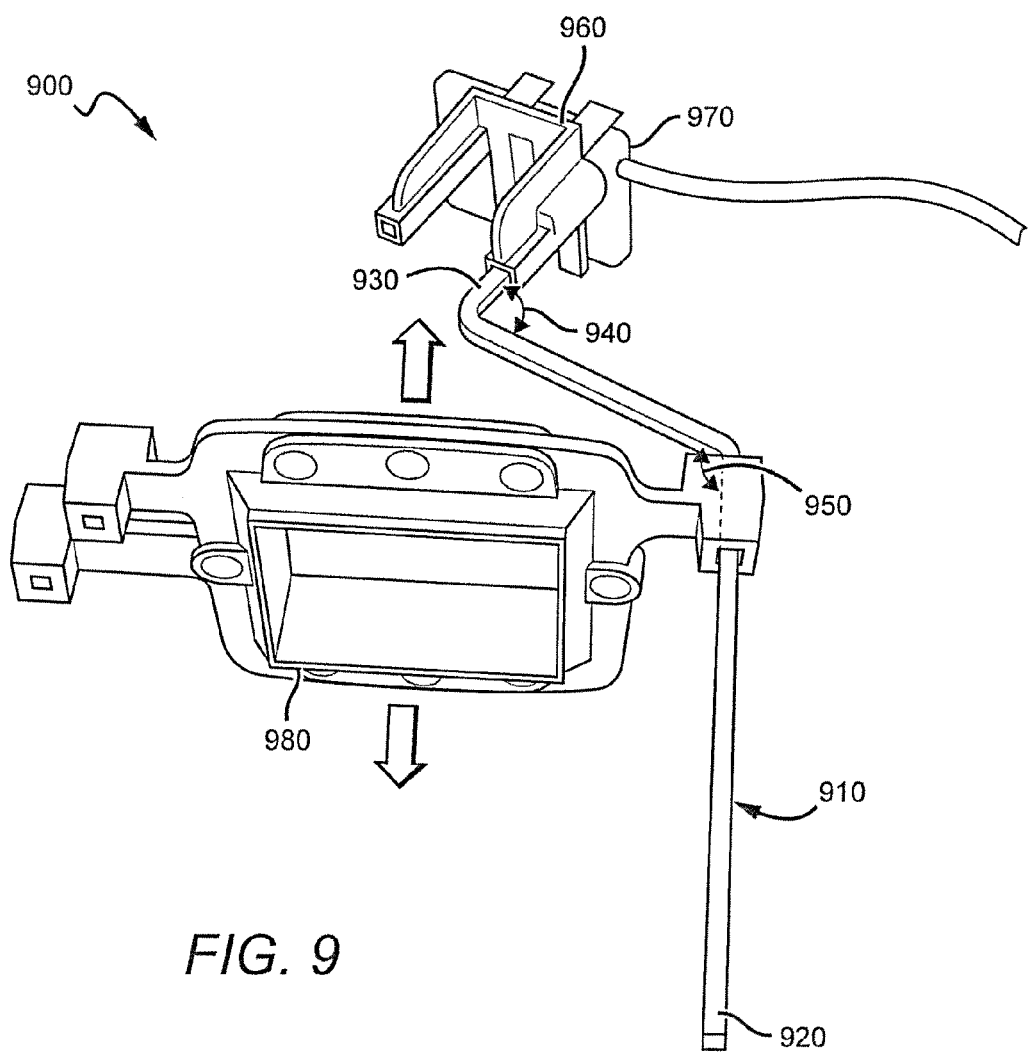

FIG. 9 shows an up close view of a positioner arm system 900 for positioning an imaging material 970 in the mouth of a patient (not shown) held by an imaging material holder 960 that includes one positioning arm 910 having a first end 920 and a second end 930, wherein the arm 910 comprises fixed arm angles that are at 90 degree angles 940 and fixed arm angles that are not at a 90 degree angle 950. This Figure also shows an aiming ring 980 that is designed to be removable from the arm 910 and slidable back and forth along the arm 910.

Figure 10:
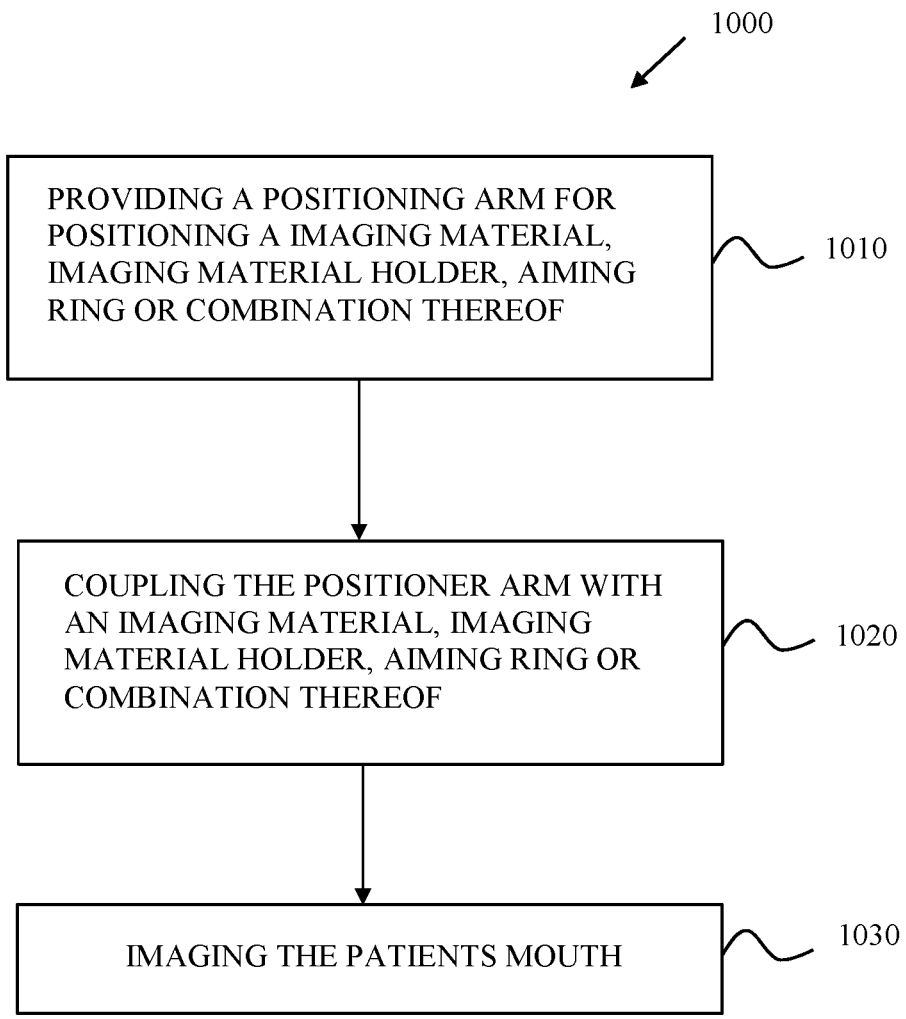

FIG. 10 shows a method 1000 of obtaining non-right angle views of a patient during x-ray imaging of the patient's mouth are also disclosed that include: providing 1010 a positioner arm for positioning an imaging material, imaging material holder, aiming ring or combination thereof, wherein the positioner arm comprises at least one positioning arm having a first end and a second end, wherein each arm comprises at least two fixed arm angles, and wherein at least one angle is not a 90 degree angle; coupling 1020 the positioner arm with an imaging material; and imaging 1030 the patient's mouth, wherein the imaging is taken at a non-right angle.

DETAILED DESCRIPTION

The obstacle for endodontists or dentists doing root canals is that conventional device holders only allow for a head on view (perpendicular) in the horizontal plate. For areas of diagnosis, and particularly in endodontics, the ability to take off angled radiographs is needed. Currently, endodontists or dentists take between 1 and 4 views per treatment tooth/teeth for diagnosis and additional during treatment, which is especially important in posterior teeth, because they are also taken for anterior teeth as well, where structures and dental instruments can be superimposed.

In practice and with conventional methods, endodontists or dentists "free hand" the angled radiographs with the current circular collimators. Ideally, the views should be standardized, but sometimes a different angle is needed (textbooks mention 20 or 30 degrees horizontally). Anteriorly, the lower teeth less commonly have superimposed canals, and as a result off angled X-rays are not required as often and when taken are less challenging to obtain the proper image. The analysis of radiographic lesions, pathology, root resorption, post perforation, anatomical structures and root canal anatomy can benefit from the additional information that off angled views can offer, and therefore, the processes and apparatus disclosed herein are important and helpful across many medical procedures.

Conventional apparatus and processes do not currently offer a solution to these problems. One possible solution is that since the collimator slips on and off easily, the practitioners can simply take it off for the many non-right-angle shots that are needed. This potential solution of removing the collimator refers to a rectangular collimator which fits over of at the end of the existing round collimator. However, with the precise aiming that is necessary with most conventional devices, free handing is not a good option.

Precise aiming is necessary with all devices but most especially with rectangular collimators. Rectangular collimation also hasn't yet been mentioned. The round collimator is never removed, unless there is a substitute rectangular collimator to replace it, although some older models did not just slip over the round collimator but instead replaced it.

The purpose of this new receptor holder arm is to produce an accurate, reproducible radiographic image using a specific defined cone-image angle of the teeth or surrounding area being examined or treated. For more accurate diagnostic information, a mesial and distal views are most helpful in revealing three dimension views. Superimposed anatomy, additional roots, or pathology can be obscured with the standard right angle radiograph. Separation of superimposed canals, position of resorptive areas and root perforations, and orientation of pathological areas are some of the benefits to an off-angled radiograph. The new arm design allows for the positioning ring or rectangular alignment ring to aim the X-ray cone at a defined angle through the teeth to expose the film/PSP plate/sensor (imaging material) held by an attached receptor bite block. The arms are designed to be used with many of the current paralleling X-ray positioning systems.

The new design in these positioning arms allow for a X-ray cone to be placed at a fixed angle to the horizontal plane of the dental arch. The arms allow for a non-perpendicular X-ray view of the arch. Examples are a 20 or 30 degrees (off of 90°) view from the mesial or from the distal.

An option with angled positioners that would hit all four areas of the mouth would satisfy most needs. In addition and in some embodiments, a film (sensor) holder designed to be used with a rubber dam in place would complete the accessories. The benefits are enhanced quality, the reduction in exposure, allowing extra views and less misses, saving time or a combination thereof.

Taking all of this information in mind, an apparatus and related methods have been developed that: a) holds x-ray film at a desired and fixed off-angle or a non-right angle in order to provide necessary information for the dental professional, and b) consistently and reliably lines up the x-ray film with the x-ray source (tube head), so as to provide the image information.

Specifically, a positioner arm for positioning an imaging material, an imaging material holder, an aiming device or a combination thereof is disclosed that includes at least one positioning arm having a first end and a second end, wherein each arm comprises at least two fixed arm angles and wherein at least one angle is not a 90 degree angle. In some embodiments, the angle closest to the first end is greater than 90 degrees. In other embodiments, the angle closest to the first end is at least 120 degrees.

In addition, methods of obtaining non-right angle views of a patient during x-ray imaging of the patient's mouth are also disclosed that include: providing a positioner arm for positioning an imaging material, wherein the positioner arm comprises at least one positioning arm having a first end and a second end, wherein each arm comprises at least two fixed arm angles, and wherein at least one angle is not a 90 degree angle; coupling the positioner arm with an imaging material; and imaging the patient's mouth, wherein the imaging is taken at a non-right angle.

In some embodiments, a contemplated apparatus—when used correctly—reproducibly and precisely locates and maintains a fixed off-angle (non-right angle) x-ray tube (unit) to film/psp plate/sensor position in relationship to the dentition and supporting structures, which is a particularly important requirement in the area of endodontics. Contemplated apparatus also hold the film in any number of angles relative to the x-ray tube head (unit).

In contemplated embodiments, a contemplated positioning arm or rigid member secures both the x-ray film/sensor holder (imaging material holder) and the x-ray tube aiming device (aiming device) in the required relationship to achieve the goals mentioned herein. In some contemplated embodiments, an imaging material, and imaging material holder, an aiming device or a combination thereof may be coupled with the positioning arm.

Rigid metal or non-metal bar formed to provide the appropriate angles. The intraoral portion affixes removable to a film/sensor holder. A commercially available aiming "ring"/device is supported on the extra oral portion to allow sliding movement, always in line with the film/sensor. The bends (shape) of the bar allows for any desired view depending what image is being looked for. The bar has bends in a two dimensional plane.

Contemplated embodiments provide a bar that is removably attachable at one end in the oral cavity to a film/psp plate/digital sensor (imaging material) holder and the extra oral end allows for an X-ray tube (unit) aiming device. The aiming device is movable (can slide closer or further) on the bar, always maintaining consistent relationship to the film/psp plate/sensor. Contemplated embodiments allow for most desired views of the imaged dentition and supporting structures. The off-angle is fixed and repeatable.

Contemplated members may be made from any suitable material based on the needs of the process, including plastic, metal, fiberglass or a combination thereof.

The devices shown in the Figures are examples that allow for mesial or distal x-ray views of the maxillary or mandibular dentition, especially useful for endodontic (root canal) treatment. However, it is clear the contemplated embodiments disclosed herein and the underlying principles can be applied to secure x-ray in any plane and/or desired angle.

FIG. 1 shows a positioner arm system 100 for positioning an imaging material (not shown) that includes one positioning arm 110 having a first end 120 and a second end 130, wherein the arm 110 comprises fixed arm angles that are at 90 degree angles 140 and fixed arm angles that are not at a 90 degree angle 150. FIG. 2 shows a positioner arm system 200 for positioning an imaging material (not shown) held by an imaging material holder 260 that includes one positioning arm 210 having a first end 220 and a second end 230, wherein the arm 210 comprises fixed arm angles that are at 90 degree angles 240 and fixed arm angles that are not at a 90 degree angle 250.

FIG. 3 shows a positioner arm system 300 for positioning an imaging material 370 held by an imaging material holder 360 that includes one positioning arm 310 having a first end 320 and a second end 330, wherein the arm 310 comprises fixed arm angles that are at 90 degree angles 340 and fixed arm angles that are not at a 90 degree angle 350. This Figure also shows an aiming ring 380 that is designed to be removable from the arm 310 and slidable back and forth along the arm 310.

Figure 4:
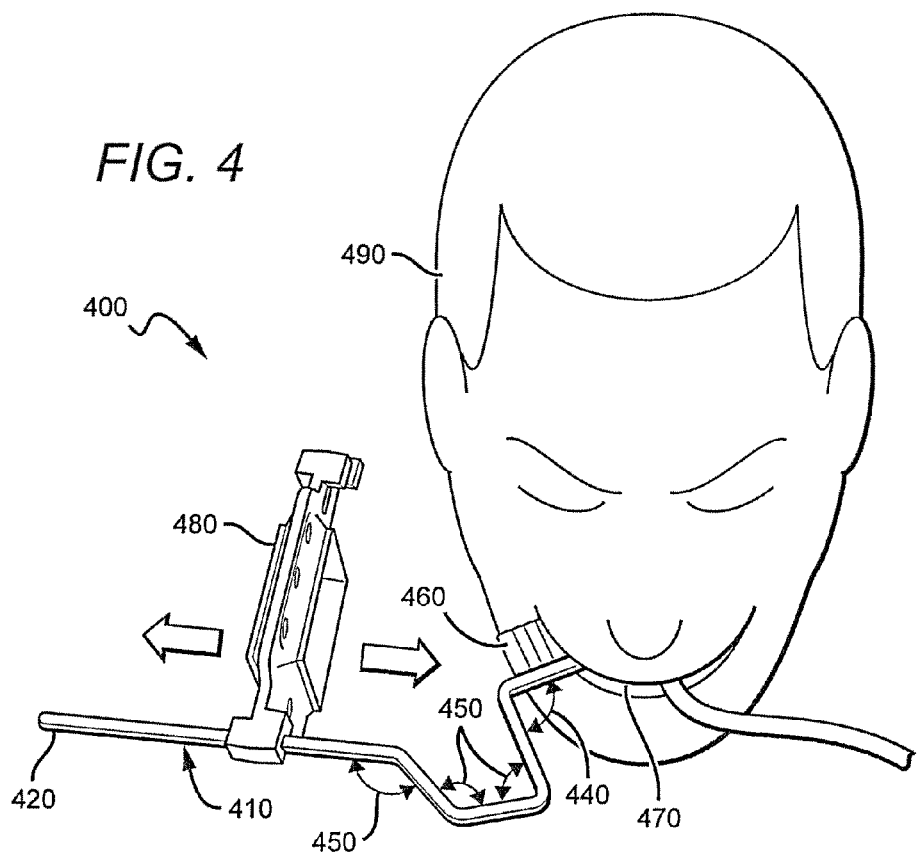
FIG. 4 shows a distal view positioner arm for film, psp plate or sensor endodontic biteblock with two additional extension rods.

FIG. 4 shows a positioner arm system 400 for positioning an imaging material 470 in the mouth of a patient 490 held by an imaging material holder 460 that includes one positioning arm 410 having a first end 420 and a second end (not shown), wherein the arm 410 comprises fixed arm angles that are at 90 degree angles 440 and fixed arm angles that are not at a 90 degree angle 450. This Figure also shows an aiming ring 480 that is designed to be removable from the arm 410 and slidable back and forth along the arm 410.

Figure 5:
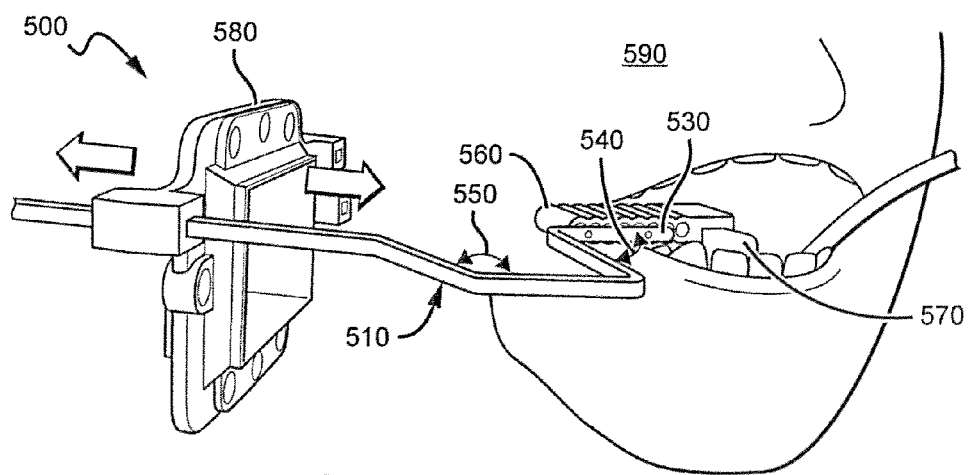
FIG. 5 shows an up close distal view of a positioner arm system 500 for positioning an imaging material 570 in the mouth of a patient 590 held by an imaging material holder 560 that includes one positioning arm 510 having a first end (not shown) and a second end 530, wherein the arm 510 comprises fixed arm angles that are at 90 degree angles 540 and fixed arm angles that are not at a 90 degree angle 550. This Figure also shows an aiming ring 580 that is designed to be removable from the arm 510 and slidable back and forth along the arm 510.

FIG. 5 shows an up close view of a positioner arm system 500 for positioning an imaging material 570 in the mouth of a patient 590 held by an imaging material holder 560 that includes one positioning arm 510 having a first end (not shown) and a second end 530, wherein the arm 510 comprises fixed arm angles that are at 90 degree angles 540 and fixed arm angles that are not at a 90 degree angle 550. This Figure also shows an aiming ring 580 that is designed to be removable from the arm 510 and slidable back and forth along the arm 510.

FIG. 6 shows a positioner arm system 600 for positioning an imaging material (not shown) that includes one positioning arm 610 having a first end 620 and a second end 630, wherein the arm 610 comprises fixed arm angles that are at 90 degree angles 640 and fixed arm angles that are not at a 90 degree angle 650. This embodiment also shows two extension rods 695 that are located near the second end 630.

FIG. 7 shows another contemplated positioner arm system 700 for positioning an imaging material (not shown) that includes one positioning arm 710 having a first end 720 and a second end 730, wherein the arm 710 comprises fixed arm angles that are at 90 degree angles 740 and fixed arm angles that are not at a 90 degree angle 750.

FIG. 8 shows a positioner arm system 800 for positioning an imaging material (not shown) that includes one positioning arm 810 having a first end 820 and a second end 830, wherein the arm 810 comprises fixed arm angles that are at 90 degree angles 840 and fixed arm angles that are not at a 90 degree angle 850. This embodiment also shows two extension rods 895 that are located near the second end 830.

FIG. 9 shows an up close view of a positioner arm system 900 for positioning an imaging material 970 in the mouth of a patient (not shown) held by an imaging material holder 960 that includes one positioning arm 910 having a first end (not shown) and a second end 930, wherein the arm 910 comprises fixed arm angles that are at 90 degree angles 940 and fixed arm angles that are not at a 90 degree angle 950. This Figure also shows an aiming ring 980 that is designed to be removable from the arm 910 and slidable back and forth along the arm 910.

FIG. 10 shows a method 1000 of obtaining non-right angle views of a patient during x-ray imaging of the patient's mouth are also disclosed that include: providing 1010 a positioner arm for positioning an imaging material, imaging material holder, aiming ring or combination thereof, wherein the positioner arm comprises at least one positioning arm having a first end and a second end, wherein each arm comprises at least two fixed arm angles, and wherein at least one angle is not a 90 degree angle; coupling 1020 the positioner arm with an imaging material; and imaging the patient's mouth, wherein the imaging is taken at a non-right angle.

Thus, specific embodiments, methods of apparatus for holding and positioning x-ray film, photostimulable phosphor plates or sensors while taking dental radiographs have been disclosed. It should be apparent, however, to those skilled in the art that many more modifications besides those already described are possible without departing from the inventive concepts herein. The inventive subject matter, therefore, is not to be restricted except in the spirit of the disclosure herein. Moreover, in interpreting the specification and claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

I claim:

1. A positioner arm for positioning an imaging material, an imaging material holder, an aiming device or a combination thereof, comprising:
   at least one positioning arm having a first end and a second end, wherein each arm comprises at least four fixed arm angles, wherein the four fixed arm angles lie in the same plane and wherein at least one angle is not a 90 degree angle.

2. The positioner arm of claim 1, further comprising at least one extension rod, at least one imaging material holder or a combination thereof located at or near the second end.

3. The positioner arm of claim 2, further comprising an imaging material coupled with the at least one extension rod, at least one imaging material holder or the combination thereof.

4. The positioner arm of claim 1, wherein the angle closest to the first end is greater than 90 degrees.

5. The positioner arm of claim 4, wherein the angle closest to the first end is at least 120 degrees.

6. The positioner arm of claim 1, further comprising an aiming device.

7. The positioner of claim 3, wherein the imaging material holder comprises a body and at least two openings defined by the body, the openings being adapted to receive at least two extension rods.

8. A method of obtaining non-right angle views of a patient during x-ray imaging of the patient's mouth, comprising:
   providing a positioner arm for positioning an imaging material, an imaging material holder, an aiming device or a combination thereof, wherein the positioner arm comprises at least one positioning arm having a first end and a second end, wherein each arm comprises least four fixed arm angles, wherein the four fixed arm angles lie in the same plane, and wherein at least one angle is not a 90 degree angle;
   coupling the positioner arm with an imaging material, an imaging material holder, an aiming device or a combination thereof; and
   imaging the patient's mouth, wherein the imaging is carried out taken at a non-right angle.

9. The method of claim 8, further comprising at least one extension rod, at least one imaging material holder or a combination thereof located at or near the second end.

10. The method of claim 9, further comprising an imaging material coupled with the at least one extension rod, at least on imaging material holder or the combination thereof.

11. The method of claim 10, wherein the imaging material holder comprises a body and at least two openings defined by the body, the openings being adapted to receive at least two extension rods.

12. The method of claim 8, further comprising at least two extension rods located at or near the second end, wherein the rods are designed to hold an imaging material, imaging material holder or a combination thereof.

13. The method of claim 8, wherein the angle closest to the first end is greater than 90 degrees.

14. The method of claim 13, wherein the angle closest to the first end is at least 120 degrees.

15. The method of claim 8, further comprising an aiming device.

16. An apparatus comprising:
   a positioning arm having four fixed arm angles that lie in a single plane, one of the four fixed arm angles being 90 degrees and three of the fixed arm angles not being 90 degrees;
   an imaging material holder positioned adjacent a first end of the positioning arm; and
   an aiming device positioned adjacent a second end of the positioning arm.

17. The apparatus of claim 16, wherein the four fixed arm angles comprise a first fixed arm angle, a second fixed arm angle, a third fixed arm angle, and a fourth fixed arm angle sequentially positioned from the first end to the second end of the positioning arm; wherein the first fixed arm angle is 90 degrees, the second fixed arm angle is an acute angle, and the third fixed arm angles is an obtuse angle, and the fourth fixed arm angle is at least 120 degrees.

18. The apparatus of claim 17, wherein straight portions define the positioning arm between the first fixed arm angle and the second fixed arm angle, between the second fixed arm angle and the third fixed arm angle, and between the third fixed arm angle and the fourth fixed arm angle.

19. The apparatus of claim 18, the positioning arm further comprises two extension rods extending from an end straight portion of the positioning arm between the first end and the first fixed arm angle, the two extension rods projecting perpendicular to the end straight portion on a side opposite a side of the generally straight portion between the first fixed arm angle and the second fixed arm angle, wherein the four fixed arm angles, the straight portions, the end straight portion, and two extension rods lie in the single plane.

20. The apparatus of claim 19, wherein the imaging material holder comprises a body having two openings, the openings being configured to receive the two extension rods, and the aiming device is configured to slide along a second end straight portion of the positioning arm from proximate the fourth fixed arm angle to the second end.

* * * * *